United States Patent
Lee et al.

(10) Patent No.: US 12,312,638 B2
(45) Date of Patent: May 27, 2025

(54) BIOMARKER FOR DIAGNOSING OR PREDICTING REACTIVITY OF OVARY TO FSH AND USE THEREOF

(71) Applicant: CHA UNIVERSITY INDUSTRY-ACADEMIC COOPERATION FOUNDATION, Pocheon-si (KR)

(72) Inventors: Kyung Ah Lee, Seoul (KR); Mi Kyoung Koong, Seoul (KR); Su Yeon Lee, Pocheon-si (KR)

(73) Assignee: CHA UNIVERSITY INDUSTRY-ACADEMIC COOPERATION FOUNDATION, Pocheon-si (KR)

(*) Notice: Subject to any disclaimer, the term of this patent is extended or adjusted under 35 U.S.C. 154(b) by 1135 days.

(21) Appl. No.: 17/269,714

(22) PCT Filed: Aug. 30, 2019

(86) PCT No.: PCT/KR2019/011161
§ 371 (c)(1),
(2) Date: Feb. 19, 2021

(87) PCT Pub. No.: WO2020/046045
PCT Pub. Date: Mar. 5, 2020

(65) Prior Publication Data
US 2021/0404001 A1    Dec. 30, 2021

(30) Foreign Application Priority Data
Aug. 31, 2018  (KR) .................. 10-2018-0104044

(51) Int. Cl.
*C07H 21/02*   (2006.01)
*C12Q 1/6883*  (2018.01)

(52) U.S. Cl.
CPC ..... *C12Q 1/6883* (2013.01); *C12Q 2600/106* (2013.01); *C12Q 2600/158* (2013.01); *C12Q 2600/178* (2013.01); *G01N 2800/367* (2013.01)

(58) Field of Classification Search
CPC .................. C12N 2310/14; C12N 15/113
See application file for complete search history.

(56) References Cited

U.S. PATENT DOCUMENTS 10,597,726 B2    3/2020   Kondou et al.
2017/0145511 A1* 5/2017  Myers ............... C12Q 1/6883

2017/0233814 A1   8/2017  Mounier et al.
2019/0048408 A1   2/2019  Natori et al.
2020/0182897 A1   6/2020  Sudo et al.

FOREIGN PATENT DOCUMENTS

| CA | 3018048 A1 * | 10/2017 | ............. C12M 1/00 |
| KR | 10-2017-0018409 A | 2/2017 | |
| KR | 10-2017-0018412 A | 2/2017 | |
| WO | WO-2016134727 A1 * | 9/2016 | ........... C12Q 1/6886 |
| WO | WO 2017/146033 A1 | 8/2017 | |
| WO | WO 2018/044979 A1 | 3/2018 | |

OTHER PUBLICATIONS

Xiao et al. (Diabetes, 63, 2014, 2631-2642).*
Ding et al. (Human Fertility, 2015, 18:1, 22-29).*
Hu et al. (Journal of Cellular Biochemistry, 2019, 120, 9964-9978).*
He et al. (Cell Physiol Biochem 2018;49:2073-2087).*
International Search Report issued on Nov. 29, 2019 in PCT/KR2019/011161 filed on Aug. 30, 2019, 2 pages.
Korean Office Action issued on Dec. 23, 2019 in Korean Patent Application No. 10-2018-0104044, 2 pages.
Lee, S.-Y. et al., "Identification of differentially expressed microRNAs and its target genes involved in FSH responsiveness in KGN cells," The 11th Congress of the Pacific Society for Reproductive Medicine (PSRM 2017), 2017, Oral Presentation 73, 2 total pages.
Ding, C.-F. et al., "Circulating microRNAs in patients with polycystic ovary syndrome," Human Fertility, vol. 18, No. 1, 2015, pp. 22-29, 9 total pages.
Leon, K. et al., "Integrating microRNAs into the complexity of gonadotropin signaling networks," Frontiers in Cell and Developmental Biology, vol. 1, Article 3, 2013, pp. 1-11.
Yarali, H. et al., "Gonadotrophin treatment in patients with polycystic ovary syndrome," Reproductive BioMedicine Online, vol. 8, No. 5, 2004, pp. 528-537.
Hu, T. et al., "The potential value of microRNA-4463 in the prognosis evaluation in hepatocellular carcinoma," Genes & Diseases, vol. 4, 2017, pp. 116-122.

(Continued)

*Primary Examiner* — Amy Rose Hudson
(74) *Attorney, Agent, or Firm* — Oblon, McClelland, Maier & Neustadt, L.L.P.

(57) ABSTRACT

Provided is a biomarker for diagnosing or predicting reactivity of an ovary to FSH and use thereof. According to a composition or a kit for diagnosing or predicting reactivity of an ovary to FSH and a method using the same according to one aspect, the degree of reactivity of the ovary may be easily diagnosed using miRNA present in blood, follicular fluid, granulosa cells, and cumulus cells, and thus it is easy to predict or diagnose symptoms or diseases caused by abnormal reactivity of the ovary to FSH.

6 Claims, 5 Drawing Sheets

Specification includes a Sequence Listing.

(56) References Cited

OTHER PUBLICATIONS

Wang, X. et al., "Roles of miR-4463 in $H_2O_2$-induced oxidative stress in human umbilical vein endothelial cells," Molecular Medicine Reports, vol. 16, 2017, pp. 3242-3252.
Cheng, W.-T. et al., "MicroRNA profiling of ovarian granulosa cell tumours reveals novel diagnostic and prognostic markers," Clinical Epigenetics, vol. 9, No. 72, 2017, pp. 1-10.
Combined Chinese Office Action and Search Report issued Nov. 10, 2023 in Chinese Patent Application No. 201980056639.2, 9 pages.
Ding, Cai-Fei, et al., "Circulating microRNAs in patients with polycystic ovary syndrome", Human Fertility, 2014, Early Online: pp. 1-8.

\* cited by examiner

SEQUENCE LISTING

<160> NUMBER OF SEQ ID NOS: 1

<210> SEQ ID NO 1
<211> LENGTH: 17
<212> TYPE: RNA
<213> ORGANISM: Artificial Sequence

```
<220> FEATURE:
<223> OTHER INFORMATION: miRNA-4463

<400> SEQUENCE: 1
gagacugggg uggggcc                                                   17
```

BIOMARKER FOR DIAGNOSING OR PREDICTING REACTIVITY OF OVARY TO FSH AND USE THEREOF

TECHNICAL FIELD

The present disclosure relates to a biomarker for diagnosing or predicting reactivity of an ovary to follicle-stimulating hormone (FSH) and use thereof.

BACKGROUND ART

Although rapid development has been made in assisted reproductive technology in recent years, pregnancy success rates after in vitro fertilization and embryo transfer remain only about 30% to 40%. The reason for such low pregnancy success rates is because the pregnancy success rates after in vitro fertilization is low in patients who have reduced ovarian function and exhibit weak responses to controlled ovarian hyperstimulation (poor ovarian response group). That is, ovarian dysfunction is considered the biggest obstacle to efforts to increase overall pregnancy rates.

In April 2011, the European Society for Hyman Reproduction and Embryology (ESHRE) provided diagnosis criteria for poor ovarian response when a responder fits into at least two of the following three items: maternal age of 40 or more or other risk factor of poor ovarian response, previous poor ovarian response (3 eggs or fewer), and abnormal ovarian reserve test results (AFC<5 to 7 or AMH<0.5-1.1 ng/mL). Although ovarian hyperstimulation is artificially applied to the poor ovarian response group, only 1 to 3 eggs are produced. As a result, in order to collect the same number of eggs from the poor ovarian response group as that of a control, injections for superovulation are required for a longer time. Thus, women have to endure increased injection stress or financial burden, which are reasons for giving up treatment for subfertility.

Therefore, appropriate treatment for successful pregnancy in the 'poor ovarian response group' showing poor response to ovarian hyperstimulation using a gonadotropic hormone remains one of the biggest challenges in the treatment of infertile patients. So far, various methods have been proposed to increase ovary-stimulating effects on patients having a 'poor ovarian response'. For example, an increase in the dose of an exogenous gonadotropin used in ovarian hyperstimulation, co-administration of clomiphene citrate and hMG, long-term co-administration or ultra-short-term administration of a gonadotropin-releasing hormone agonist, use of a gonadotropin-releasing hormone antagonist, and administration of a growth hormone may be used. However, clinical results of these methods are far less than clinical results observed in a normal response group. Also, methods of using a GnRH agonist or a GnRH antagonist have been used, and methods of increasing doses of other gonadotropins or further adding various substances such as DHEA, Letrozole, and L-arginine have been reported. In addition, although successful pregnancies through the activation of primordial follicles in ovary tissue using a PTEN inhibitor, induction of tissue-engineered bioimplant and follicle development, harvesting of mature eggs, and in vitro fertilization and embryo transfer have been reported, it is difficult to apply these processes in general as success rates are very low despite very complex processes.

Meanwhile, poor ovarian response refers to a low response of an ovary to injections for superovulation for in vitro fertilization, i.e., production of 3 eggs or fewer although eggs were collected after injections for superovulation or a case in which such results are expected based on various diagnosis results. In the case of the poor ovarian response group, most of the ovaries have significantly lowered function and pregnancy rates are generally low. In general, the poor ovarian response is diagnosed in consideration of the number of growing follicles observed by ultrasound scanning during stimulation by gonadotropin (gonadotropic hormone). However, because there is no specific manual for diagnosis (measurement time, and diameter of growing follicle), the poor ovarian response is diagnosed based on the number of collected eggs (3 to 6). In this regard, low response of the ovary to gonadotropin may be a temporary phenomenon and may not recur even after adjusting a dose of the hormone or even administering the same dose. According to a published study, it has been reported that about ⅓ of women with poor ovarian responses show normal superovulation in the next cycle. As such, the phenomenon in which various variations may be found in the number of growing follicles according to cycles is a factor that should be considered in diagnosis of poor ovarian response.

As described above, the 'declined ovarian function' is defined using different criteria, and thus efforts to discover a biomarker for preventing, diagnosing, or predicting poor ovarian response with ovarian dysfunction or premature menopause are required.

DESCRIPTION OF EMBODIMENTS

Technical Problem

Provided is a biomarker capable of diagnosing or predicting reactivity of an ovary to follicle-stimulating hormone (FSH), and more particularly, a composition or kit including an agent for measuring an expression level of miRNA-4463 or a mimic thereof, a use of the miRNA-4463 or a mimic thereof, a method of diagnosing reactivity of an ovary to FSH using the same, or a method of providing information for diagnosing or predicting reactivity of an ovary to FSH.

Provided is a biomarker capable of diagnosing or predicting ovarian dysfunction or premature menopause, and more particularly, a composition or kit including an agent for measuring an expression level of miRNA-4463 or a mimic thereof, a use of the miRNA-4463 or a mimic thereof, a method of diagnosing ovarian dysfunction or premature menopause using the same, or a method of providing information for diagnosing or predicting ovarian dysfunction or premature menopause.

Solution to Problem

According to an aspect of the present disclosure, provided is a composition for diagnosing or predicting reactivity of an ovary to follicle-stimulating hormone (FSH), the composition including an agent for measuring an expression level of at least one selected from microRNA-4464 (miRNA-4463), miRNA-130-3p, miR-185-5p, miRNA-329-3p, and a mimic thereof.

According to another aspect of the present disclosure, provided is a method of diagnosing or predicting reactivity of an individual having ovarian dysfunction to FSH, ovarian dysfunction, or premature menopause, the method including measuring an expression level of at least one selected from miRNA-4463, miRNA-130-3p, miR-185-5p, miRNA-329-3p, and a mimic thereof in a sample isolated from the individual.

The method of diagnosing or predicting reactivity of the individual having ovarian dysfunction to FSH, ovarian dysfunction, or premature menopause includes: measuring an expression level of at least one selected from miRNA-4463, miRNA-130-3p, miR-185-5p, miRNA-329-3p, and a mimic thereof in a sample isolated form the individual; comparing the measured expression level with an expression level of the same gene measured in a control; and determining that the reactivity of the individual to FSH is poor when the expression level of the sample is less or more than the expression level of the control.

According to another aspect of the present disclosure, provided is a Use for diagnosing or predicting reactivity of an ovary to follicle-stimulating hormone (FSH), of an agent for measuring an expression level of at least one selected from miRNA-4463, miRNA-130-3p, miR-185-5p, miRNA-329-3p, and a mimic thereof.

As used herein, the term "microRNA (miRNA or mir)" includes not only miRNA represented by a specific nucleotide sequence (or SEQ ID NO:) but also a precursor of the miRNA (pre-miRNA), a primary transcript (pri-miRNA), and any miRNA having biological functions equivalent thereto, such as a homolog (or ortholog), a variant such as gene polymorphism, and a derivative. The precursor, primary transcript, homolog, variant, or derivative may be identified based on miRBase release 20 (http://WWW.mirbase.org/).

Also, throughout the specification, miRNA may be a gene product of mir gene which includes mature miRNA (e.g., a non-coding RNA of 15 to 25 base pairs or 19 to 25 base pairs involved in inhibition of translation of mRNA or a miRNA precursor or transcript (e.g., pre-miRNA or pri-miRNA).

In an embodiment, the mimic may be one of: a) a polynucleotide including a mature sequence of miRNA; b) a polynucleotide including a sequence of a precursor of miRNA (pre-miRNA); and c) a polynucleotide including a primary transcript of miRNA (pri-miRNA).

In an embodiment, the miRNA-4463 mimic may be one of: a) a polynucleotide including a mature sequence of miRNA-4463; b) a polynucleotide including a sequence of a precursor of miRNA-4463 (pre-miRNA), and c) a polynucleotide including a primary transcript of miRNA-4463 (pri-miRNA).

In an embodiment, the miRNA-4463 or the miRNA-4463 mimic may be a polypeptide having a SEQ ID NO: 1. The sequence may be modified to some extent in diagnosing the reactivity of an ovary to FSH. It will be obvious to those skilled in the art that a nucleotide sequence, in which a homology of 80% or more, preferably 90% or more, more preferably 95% or more, and the most preferably 98% is maintained by artificial modification, is equivalent to the nucleotide sequence as long as significant comparison between expression levels of a normal individual and an individual with no reactivity of an ovary are possible as a marker for predicting reactivity of an ovary to FSH according to the present disclosure.

As used herein, the term "reactivity of an ovary to FSH" refers to whether the ovary responds to FSH or the degree of response thereof. In an embodiment, the reactivity of an ovary to FSH may be measured by measuring reactivity of granulosa cells to FSH. As used herein, the term "granulosa cells" may refer to granulosa cells in ovarian follicles. For the successful maturation of an egg, normal division and growth of cumulus cells and granulosa cells balanced with the egg are very important. However, female eggs cannot be directly used in research, studies should be carried out on granulosa cells in follicles that play an important role in maturation of the eggs and located around the eggs. However, granulosa cells have been known as difficult cells to study since luteinization occurs immediately after the granulosa cells are released form follicles.

The reactivity of an ovary to FSH may refer to whether the ovary produces estrogen in response to FSH or a degree of estrogen generation and may be evaluated, for example, by measuring whether granulosa cells produce estrogen in response to FSH or the degree of estrogen generation. The granulosa cells have been known to play a role in producing estrogen in response to FSH and control development of a follicle. Abnormal reactivity to FSH may cause abnormal estrogen generation, resulting in ovarian dysfunction or premature menopause. As a result, diseases caused by decline in ovarian function, e.g., ovarian dysfunction or premature menopause may be diagnosed or predicted by diagnosing or predicting reactivity of an ovary to FSH in advance.

In an embodiment, a high expression level of miRNA-4463 or a mimic thereof may indicate no reactivity or a low-level reactivity of an ovary to FSH.

In an embodiment, a low expression level of miRNA-4463 or a mimic thereof may indicate the existence of reactivity or a high-level reactivity of an ovary to FSH.

As used herein, the term "diagnosing" refers to identifying the presence or characteristics of a pathological condition. Throughout the specification, the diagnosing may be understood as identifying reactivity of an ovary to FSH in an individual.

As used herein, the term "marker" or biomarker is a substance used to predict reactivity of an ovary to FSH and includes organic biomolecules exhibiting different reactivities to FSH in granulosa cells, such as metabolites, polypeptides, proteins or nucleic acids, genes, lipids, glycolipids, glycoproteins, or sugars. Throughout the specification, the marker may be miRNA-4463 or a mimic thereof.

As used herein, the term "agent for measuring an expression level of nucleic acids" refers to an agent used for a method of measuring an expression level of m RNA transcribed from a target gene to identify expression of the target gene contained in a sample. The "agent" means an agent used for a method of identifying expression of miRNA-4463 or a mimic or fragment thereof contained in sample, preferably a primer or probe that is able to specifically bind to a target gene used in methods such as reverse transcription-polymerase chain reaction (RT-PCR), competitive RT-PCR, real-time RT-PCR, RNase protection assay (RPA), Northern blotting, and DNA chip assay, but is not limited thereto. As used herein, the term "primer" refers to a short nucleic acid strand having a free 3' hydroxyl group, capable of forming a base pair with a complementary template and serving as a starting point for template strand replication. The primer is able to initiate DNA synthesis in the presence of a reagent for polymerization (i.e., DNA polymerase or reverse transcriptase) and four different nucleoside triphosphates and in an appropriate buffer at a suitable temperature. As used herein, the term "probe" refers to a fragment of a nucleic acid, such as RNA or DNA, which may specifically bind to a gene or mRNA and includes several bases to several hundred bases, and may be prepared in the form of an oligonucleotide probe, a single-stranded DNA probe, a double-stranded DNA probe, and an RNA probe and labeled for easy detection. The primer or probe may be chemically synthesized using a phosphoramidite solid support method or any other method well known in the art. Their nucleotide sequences may also be modified using various methods well known in the art. Examples of the modification may include, but are not limited to, methylation, capping, substitution of natural nucleotides with one or more homologs, and alternation between nucleotides, such as alternation into uncharged linkers (e.g., methyl phosphonate, phosphotriester, phosphoroamidate, and carbamate) or charged linkers (e.g., phosphorothioate and phosphorodithioate).

The miRNA-4463 may be a substance targeting mRNA of cytochrome P450 family 19 subfamily A member 1 (CYP19A1) or ESR1 (ER-α). CYP19A1 is an estrogen synthesizing enzyme (aromatase) that finally synthesizes 17β-estrogen in granulosa cells. 17β-estrogen is a steroid hormone, as one of the estrogens substantially having biological functions, and controls gene expression via ESR1 (ER-α) and ESR2 (ER-β) which are intracellular or nuclear receptors.

The miRNA-4463 may be a substance inhibiting synthesis of estrogen in granulosa cells. Specifically, the synthesis of estrogen may be inhibited by targeting mRNA of cytochrome P450 family 19 subfamily A member 1 (CYP19A1) or ESR1 (ER-α) in granulosa cells.

Diseases caused by decline in ovarian function, e.g., ovarian dysfunction or premature menopause, may be diagnosed or predicted in the composition by diagnosing or predicting reactivity of an ovary to FSH. The "ovarian dysfunction" occurs when woman's ovaries do not function normally and may be classified into anovulatory dysfuncdysfunc uterine bleeding (DUB), ovu-latory DUB, premature menopause, ovulatory irregular menstrual cycles, insufficient luteinization, anovulatory irregular menstrual cycles, and the like. The ovarian dysfunction may be used interchangeably with the poor ovarian response and may refer to a state in which 3 eggs or fewer are produced even after injections for superovulation were applied for in vitro fertilization or a state in which such results are expected. The "premature menopause" refers to menopause that occurs below the median age of natural menopause. As women age, functions of ovaries stop, so that production of estrogen decreases and menstrual periods stop permanently. This phenomenon is referred to as menopause. Although menopause normally occurs between about 45 to 56 years of age, premature menopause is clinically defined as menopause occurring before age 40 and has symptoms of an increase in FSH secretion and a decrease in estrogen secretion in patients.

The composition may further include a sample required for predicting reactivity of an ovary to FSH.

According to another aspect of the present disclosure, provided is a kit for diagnosing or predicting reactivity of an ovary to follicle-stimulating hormone (FSH), the kit including an agent for measuring an expression level of microRNA-4464 (miRNA-4463) or a mimic of miRNA-4463.

In an embodiment, the kit may be an RT-PCR kit, but is not limited thereto. The RT-RCP kit may include not only a pair of primers specific to the gene, but also a test tube or any other appropriate container, a reaction buffer (various pHs and magnesium concentrations), deoxynucleotide (dNTPs), Taq-polymerase and enzymes such as a reverse transcriptase, DNase, RNAse inhibitor, DEPC-water, sterile water, and the like. Also, the kit may include a pair of primers specific to a gene used as a quantitative control. The kit may include an agent, a device, and a computer including an algorithm to measure the level of the miRNA-4463 or miRNA-4463 mimic so as to reveal relation between a result of the level of the marker measured by the algorithm and reactivity of an ovary to FSH.

In the kit, any known algorithm selected from, but not limited to, linear or nonlinear regression algorithm; linear or nonlinear classification algorithm; ANOVA; neural network algorithm; genetic algorithm; support vector machine algorithm; hierarchical analysis or clustering algorithm; hierarchical algorithms using decision trees, or Kernel principal component analysis algorithm; Markov Blanket algorithm; recursive feature elimination or entropy-based recursive feature elimination algorithms; a plurality of algorithms arranged in a committee network; and forward floating search or backward floating search algorithm, may be used.

According to another aspect of the present disclosure, provided is a method of providing information required for diagnosing or predicting reactivity of an ovary to follicle-stimulating hormone (FSH), the method including: measuring an expression level of miRNA-4463 or a miRNA-4463 mimic in a biological sample isolated from an individual; and comparing the expression level with an expression level of miRNA-4463 or a miRNA-4463 mimic measured in a control.

The individual may be a mammal including a human.

As used herein, the term "biological sample" refers to a sample obtained from a living organism. The biological sample may be blood, plasma, platelet, serum, ascites, bone marrow fluid, lymph fluid, saliva, tear, mucosal fluid, amniotic fluid, follicular fluid, granulosa cells, cumulus cells, or any combination thereof. When the biological sample is blood or plasma, there is no need to excise organs from an individual by using easily collectable blood or plasma as a specimen, and thus the specimen may be simply analyzed without causing any inconvenience to the individual. In addition, when the biological sample is follicular fluid, granulosa cells, or cumulus cells, the sample, which is collected together with eggs during an in vitro fertilization procedure and remains after collecting the eggs required for the procedure, may be used, and thus a process for obtaining the sample is relatively easy. Therefore, prediction may be easily performed by using miRNA contained in easily collectable blood, follicular fluid, granulosa cells, or cumulus cells as a marker capable of predicting reactivity of an ovary to the hormone.

In the method, ovarian dysfunction or premature menopause may be diagnosed or predicted by diagnosing or predicting reactivity of an ovary to FSH.

In the method, clinical information in addition to the marker of the individual may further be used to provide information for diagnosing or predicting reactivity of an ovary to FSH, in addition to marker analysis results. Such clinical information may include ovarian reserve test results, and the like.

According to another aspect of the present disclosure, provided is a method of screening an agent for preventing or treating declined reactivity of an ovary to FSH, the method including: administering a candidate substance predicted to prevent or treat decline in the reactivity of the ovary to FSH; and measuring an expression level of miR-4463 or a mimic thereof.

The method includes: (a) measuring an expression level of miRNA-4463 or a mimic thereof in a biological sample isolated from an individual in which reactivity of an ovary to FSH is declined as a control; (b) administering a candidate substance predicted to treat the declined reactivity of an ovary to FSH in the individual; (c) measuring an expression level of miRNA-4463 or a mimic thereof in the biological sample isolated from the individual administered with the candidate substance as an experimental group; and (d) determining the candidate substance as an agent for preventing or treating the declined reactivity of the ovary to FSH when the expression level of miRNA-4463 or a fragment thereof measured in the experimental group is lower than that measured in the control upon comparison results therebetween.

Advantageous Effects of Disclosure

According to the composition or kit for diagnosing or predicting reactivity of an ovary to FSH, and a method thereof using the same, symptoms or diseases caused by abnormal reactivity of the ovary to FSH may be easily predicted or diagnosed by simply diagnosing the degree of reactivity of the ovary to FSH using miRNA present in blood, follicular fluid, granulosa cells, or cumulus cells.

MODE OF DISCLOSURE

Hereinafter, the present disclosure will be described in more detail with reference to the following examples. However, the following experimental examples are merely presented to exemplify the present disclosure, and the scope of the present disclosure is not limited thereto.

Example 1 Conformation of Effect of FSH on Granulosa Cells 1.1. Cell Line for Use In 2001, Dr. Nishi and his team in Japan constructed KGN cells, which are human ovarian granulosa-like tumor cell lines, exhibiting secretion characteristics of a female gonadal hormone similar to granulosa cells, from ovarian granulosa carcinoma. Since then, KGN cells have been used for studies that require a large amount of cells such as screening of characteristics of female granulosa cells and reaction to endocrine disruptors. According to the present disclosure, prior to studies for various characteristics of female granulosa cells that are difficult to obtain, a granulosa cell culture system was constructed and a series of studies were performed to accumulate basic DATA required for utilization of various germ cells required to improve female fertility. The present inventors used KGN cells, provided by RIKEN of Japan, a human granulosa cell line expressing a follicle-stimulating hormone receptor (FSHR) in a high level.

1.2. Identification of Change in FSHR Expression by FSH Treatment in Human Granulosa Cell Line An experiment was performed as follows by treating the KGN cell line, in which the expression of FSHR was reduced, with FSH to identify a change induced by FSH in expression of FSHR. First, the KGN cell line was treated with FSHR siRNA to reduce the expression of FSHR in the cell line. The treated cell line was further treated with follicle-stimulating hormone (FSH), and then a change in expression of FSHR mRNA was identified by RT-PCR and a change in the expression of FSHR protein was identified by western blotting.

Figure 1:
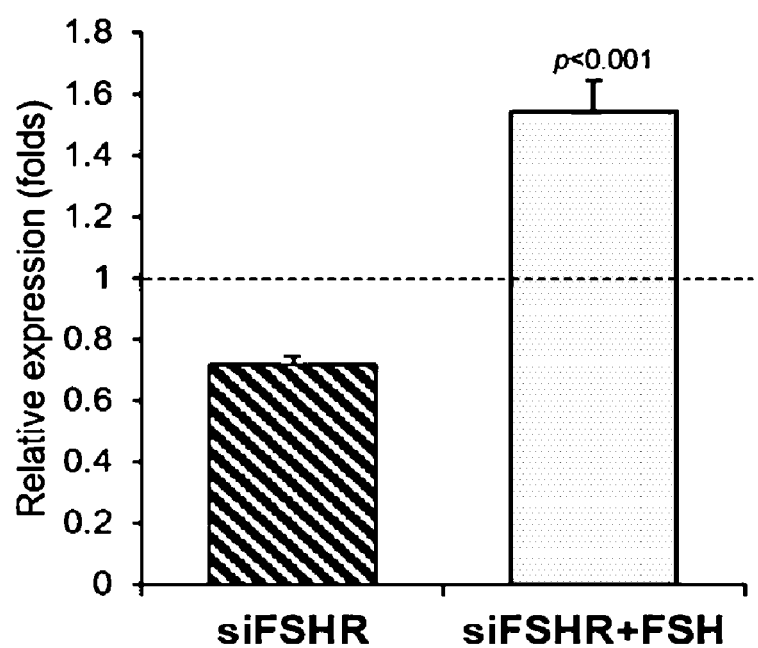
FIG. 1 is a graph illustrating expression levels of FSHR mRNA in a KGN cell line in which expression of FSHR is suppressed (siFSHR) and in the KGN cell line further treated with FSH (siFSHR+FSH), identified by RT-PCR.

FIG. 1 is a graph illustrating expression levels of FSHR mRNA in a KGN cell line in which expression of FSHR is suppressed (siFSHR) and in the KGN cell line further treated with FSH (siFSHR+FSH) identified by RT-PCR.

Figure 2:
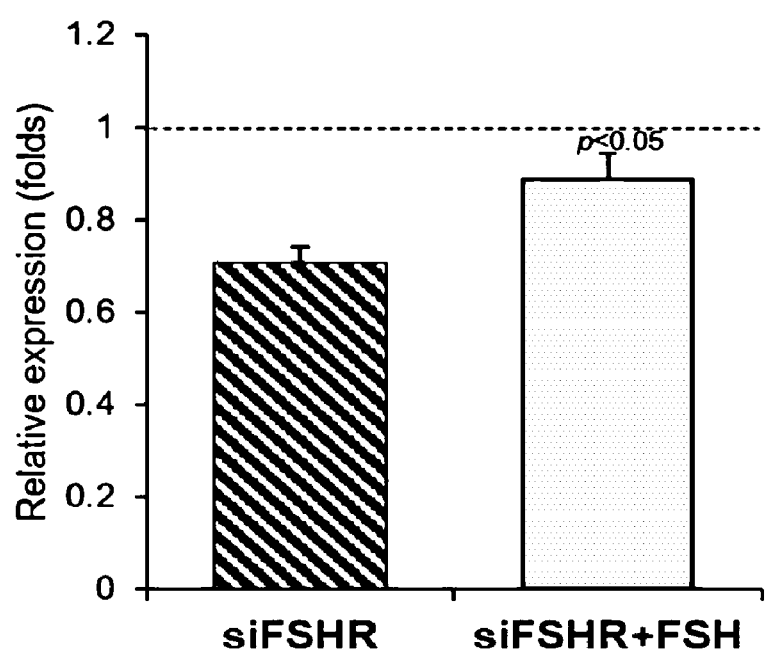
FIG. 2 is a graph illustrating expression levels of FSHR protein in a KGN cell line in which expression of FSHR is suppressed (siFSHR) and in a KGN cell line further treated with FSH (siFSHR+FSH), identified by western blotting.

FIG. 2 is a graph illustrating expression levels of FSHR protein in a KGN cell line in which expression of FSHR is suppressed (siFSHR) and in a KGN cell line further treated with FSH (siFSHR+FSH) identified by western blotting.

As shown in FIGS. 1 and 2, in the KGN cell line in which the expression of FSHR was suppressed, relative expression levels of FSHR mRNA and FSHR protein were low and significantly increased again after FSH treatment.

Therefore, FSH has an effect of restoring the decreased expression level of FSHR on human granulosa cells.

1.3. Identification of Change in Estrogen Expression by FSH Treatment in Human Granulosa Cell Line An experiment was performed as follows to identify a change induced by FSH in synthesis of estrogen by treating the KGN cell line, in which expression of FSHR was reduced, with FSH. First, the KGN cell line was treated with FSHR siRNA to reduce the expression of FSHR in the cell line. The treated cell line was further treated with follicle-stimulating hormone (FSH), and then an amount of estrogen secreted into a culture solution was identified by ELISA.

Figure 3:
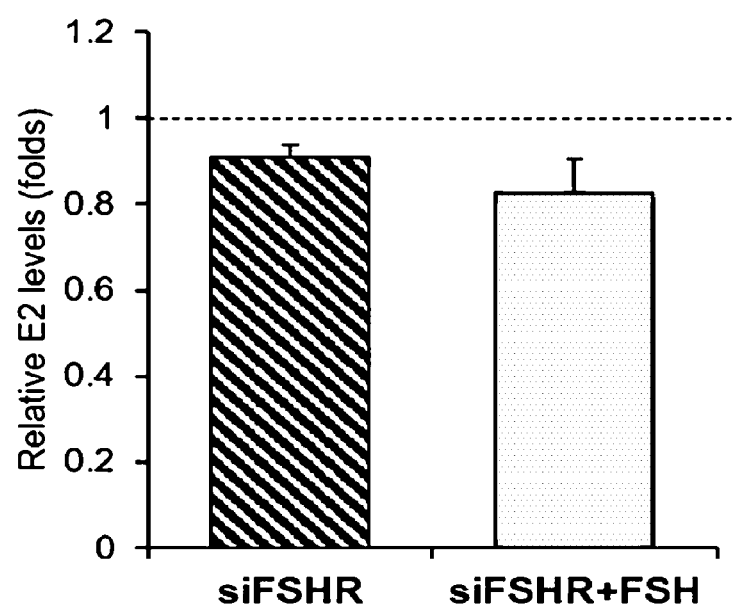
FIG. 3 is a graph illustrating amounts of estrogen secreted into a culture solution of a KGN cell line in which expression of FSHR is suppressed (siFSHR) and a culture solution including the KGN cell line further treated with FSH (siFSHR+FSH), identified by ELISA. E2: estrogen.

FIG. 3 is a graph illustrating amounts of estrogen secreted into a culture solution of a KGN cell line in which expression of FSHR is suppressed (siFSHR) and a culture solution including the KGN cell line further treated with FSH (siFSHR+FSH) identified by ELISA. In the graph, E2 is estrogen.

As shown in FIG. 3, the amount of estrogen secreted into the culture solution from the KGN cell line in which the expression of FSHR was suppressed was low but was not recovered even after further treating the cell line with FSH. Thus, it was confirmed that estrogen is not produced because reactivity of the granulosa cells to FSH has decreased when FSHR is not expressed.

Example 2 Derivation of Biomarker for Diagnosing Ovarian Dysfunction

To derive a biomarker for diagnosing ovarian dysfunction, miRNA expressed in different levels according to reactivity to FSH was identified by miRNA microarray. Total RNA of the cells was extracted and the 5'-terminal phosphate group was removed therefrom by Calf Intestinal Alkaline Phosphatase (CIP), and then the total RNA was labeled with Cy3 fluorescent dye. The labeled RNA and a microarray slide were sufficiently reacted at 56° C. for 16 hours and washed. The slide was scanned using an Agilent G2565CA Microarray Scanner System and fluorescence intensity was quantified so as to analyze difference of miRNA expression between groups. Quantified values were analyzed after normalization using GeneSpring GX 13.1.

Specifically, in the case where the KGN cell line, as a control, and the KGN cell line in which expression of FSHR is suppressed, were treated with FSH, respectively, a list of miRNAs increasing or decreasing twice or more by treatment of FSH was identified by microarray. As a result, 4 miRNAs (miR-130a-3p, miR-329-3p, miR-4463, and miR-185-5p) in total were obtained.

Target genes of these miRNAs were identified by 8 databases (miRWalk, PITA, miRanda, RNA22, miRDB, RNAhybrid, Pictar2, and Targetscan). As a result, a list of 725 target genes commonly regulated by miR-130a-3p, miR-329-3p, miR-4463, and miR-185-5p was obtained.

DAVID functional annotation bioinformatics were used to analyze signaling pathways including the obtained 725 target genes, and top 10 signaling pathways including a large number of the target genes are shown in Table 1 below.

TABLE 1

| Rank | Term | No. of genes | P-value |
|---|---|---|---|
| 1 | Pathways in cancer | 36 | 1.70E−05 |
| 2 | HTLV-1 infection | 27 | 2.40E−05 |
| 3 | PI3K-Art signaling pathway | 23 | 3.30E−02 |
| 4 | cGMP-PKG signaling pathway | 22 | 5.50E−06 |
| 5 | Ras signaling pathway | 22 | 5.10E−04 |
| 6 | Endocytosis | 20 | 1.20E−02 |
| 7 | PKA/cAMP signaling pathway | 19 | 1.60E−03 |
| 8 | MAPK signaling pathway | 19 | 2.10E−02 |
| 9 | Hippo signaling pathway | 17 | 5.80E−04 |
| 10 | Transcriptional misregulation in cancer | 17 | 1.80E−03 |

As shown in Table 1, it was confirmed that the top 10 signaling pathways include PI3K-Akt signaling pathway, Ras signaling pathway, and PKA/cAMP signaling pathway related to FSH signaling.

Therefore, it was concluded that miRNAs expressed in different levels according to reactivity to FSH (miR-130a-3p, miR-329-3p, miR-4463, and miR-185-5p) are actually related to the FSH signaling pathway.

Then, a list of target gens of FSH and genes related to ovarian stimulation was identified in a plurality of theses, e.g., Dr. Joanne Richard (2010), or Sigma Altmae (2011), and is shown in Table 2 below.

TABLE 2

| miRNAs | Genes |
|---|---|
| miR-130a-3p | CCND2, SOD2, PGR |
| miR-185-5p | PGR, MTHFR, SLC19A1, TCN2 |
| miR-329-3p | GSK3β, PGR |
| miR-4463 | CCND2, GSK3β, CYP12A1, MTHFR, PGR, ESR1 |

As shown in Table 2, it was confirmed that among them, a large number of target genes of miR-130a-3p, miR-329-3p, miR-4463, and miR-185-5p are included in the list. Particularly, CYP19A1 that is aromatase synthesizing estrogen in granulosa cell and ESR1 (ER-α) that is an estrogen receptor were derived as target genes of miR-4463.

To sum up, because increased expression of miR-130a-3p, miR-329-3p, miR-4463, and miR-185-5p by twice or more was confirmed between the granulosa cell lines having reduced reactivity to FSH by inhibiting FSHR and the granulosa cell line having restored reactivity by further treating the cell line with FSH, it may be confirmed that miRNAs related to reactivity to FSH are miR-130a-3p, miR-329-3p, miR-4463, and miR-185-5p. Furthermore, as a result of identifying target genes of miR-130a-3p, miR-329-3p, miR-4463, and miR-185-5p, a large number of FSH target genes and genes related to ovarian stimulation are included in the list. Thus, it may be expected that the four miRNAs paly important roles in ovarian functions. Particularly, it was confirmed that CYP19A1 and ESR1 (ER-α) which regulate estrogen synthesis or biological function are target genes of miR-4463 in granulosa cells.

Example 3 Verification of Biomarker

Decrease in expression of CYP19A1 and ESR1 (ER-α) in granulosa cells by treatment with MiR-4463 was identified as follows. To identify whether secretion of estrogen is changed by treatment with miR-4463 in the granulosa cells, expression levels of CYP19A1, ER-α, and ER-β proteins were identified in untreated KGN cell line (MOCK), miR-4463 mimic-treated KGN cell line (miR-4463 mimic), and miR-4463 inhibitor-treated KGN cell line (miR-4463 inhibitor) by western blotting.

Figure 4:
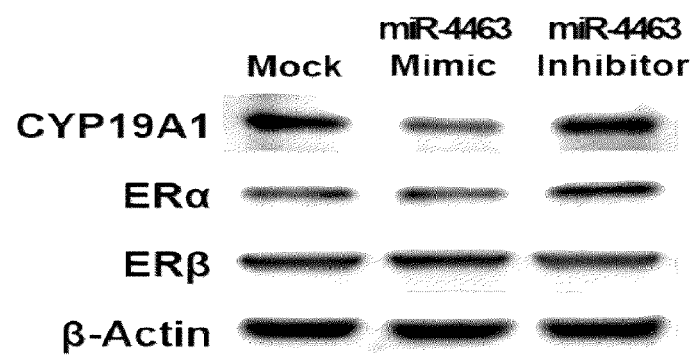
FIG. 4 is a graph illustrating expression levels of CYP19A1, ER-α, and ER-β proteins in an untreated KGN cell line (MOCK) as a control, an miR-4463 mimic-treated KGN cell line (miR-4463 mimic), and an miR-4463 inhibitor-treated KGN cell line (miR-4463 inhibitor), identified by western blotting.

FIG. 4 is a graph illustrating expression levels of CYP19A1, ER-α, and ER-β proteins in an untreated KGN cell line (MOCK) as a control, an miR-4463 mimic-treated KGN cell line (miR-4463 mimic), and an miR-4463 inhibitor-treated KGN cell line (miR-4463 inhibitor) identified by western blotting.

As shown in FIG. 4, the expression levels of CYP19A1 and ER-α were significantly reduced by the miR-4463 mimic, and the expression level of the miR-4463 inhibitor-treated cell line was higher than that of the control.

Also, a change in estrogen secretion by treatment with miR-4463 in granulosa cells was identified as follows. Untreated KGN cell line (MOCK), miR-4463 mimic-treated KGN cell line (miR-4463 mimic), and miR-4463 inhibitor-treated KGN cell line (miR-4463 inhibitor) were cultured and amounts of estrogen secreted into culture solutions were identified by ELISA.

Figure 5:
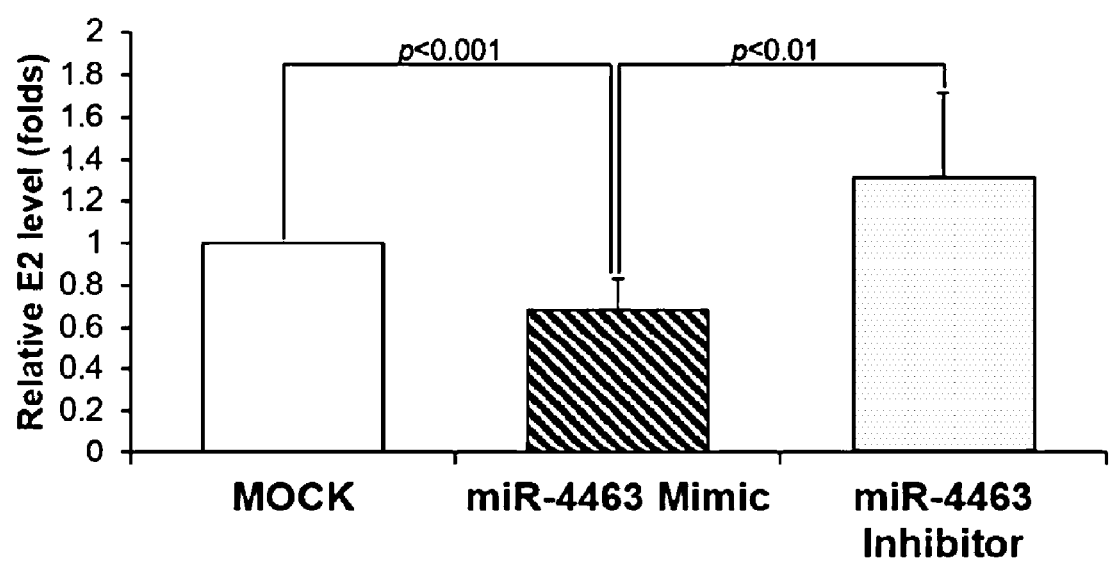
FIG. 5 is a graph illustrating amounts of estrogen secreted into culture solutions of in an untreated KGN cell line (MOCK) as a control, an miR-4463 mimic-treated KGN cell line (miR-4463 mimic), and an miR-4463 inhibitor-treated KGN cell line (miR-4463 inhibitor), identified by ELISA.

FIG. 5 is a graph illustrating amounts of estrogen secreted into culture solutions of an untreated KGN cell line (MOCK) as a control, an miR-4463 mimic-treated KGN cell line (miR-4463 mimic), and an miR-4463 inhibitor-treated KGN cell line (miR-4463 inhibitor), identified by ELISA. In the graph, E2 is estrogen.

As shown in FIG. 5, secretion of estrogen was significantly by the miR-4463 mimic, and the secretion of estrogen treated with the miR-4463 inhibitor was higher than that of the control.

That is, miR-4463 is involved in secretion of estrogen of granulosa cells by regulating expression of CYP19A1 and ESR1 (ER-α). Therefore, reactivity of an ovary to FSH may be diagnosed or predicted by identifying reactivity of miR-4463 to FSH in granulosa cells.

The invention claimed is:

1. A composition for diagnosing or predicting reactivity of an ovary to follicle-stimulating hormone (FSH), comprising an agent for measuring an expression level of microRNA-4463 (miRNA-4463) and microRNA-329-3p, or an expression level of mimic thereof, wherein the agent is a primer or a probe.

2. The composition of claim 1, wherein the miRNA-4463 mimic is at least one selected from the group consisting of a polynucleotide comprising a mature sequence of miRNA-4463;

a polynucleotide comprising a sequence of a precursor of miRNA-4463 (pre-miRNA), and a polynucleotide comprising a primary transcript of miRNA-4463 (pri-miRNA).

3. The composition of claim 1, wherein the miRNA-4463 has SEQ ID NO: 1.

4. The composition of claim 1, wherein the miRNA-4463 targets mRNA of cytochrome P450 family 19 subfamily A member 1 (CYP19A1) or ESR1 (ER-α).

5. The composition of claim 1, wherein the miRNA-4463 inhibits synthesis of estrogen in granulosa cells.

6. The composition of claim 1, wherein ovarian dysfunction or premature menopause is diagnosed or predicted by diagnosing or predicting the reactivity of the ovary to FSH.

* * * * *